(12) United States Patent
Ahmed et al.

(10) Patent No.: US 11,624,664 B2
(45) Date of Patent: Apr. 11, 2023

(54) PH PHOTOTHERMAL SPECTROMETER AND PERFORMING PH PHOTOTHERMAL SPECTROSCOPY

(71) Applicant: Government of the United States of America, as represented by the Secretary of Commerce, Gaithersburg, MD (US)

(72) Inventors: Zeeshan Ahmed, Washington, DC (US); Matthew Robert Hartings, Gaithersburg, MD (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 307 days.

(21) Appl. No.: 17/110,996

(22) Filed: Dec. 3, 2020

(65) Prior Publication Data
US 2022/0099503 A1 Mar. 31, 2022

Related U.S. Application Data

(60) Provisional application No. 63/084,313, filed on Sep. 28, 2020.

(51) Int. Cl.
*G01K 11/32* (2021.01)
*G01N 21/88* (2006.01)
*G01N 21/80* (2006.01)
*A61B 5/145* (2006.01)
*G01N 21/77* (2006.01)

(52) U.S. Cl.
CPC .......... *G01K 11/32* (2013.01); *A61B 5/14539* (2013.01); *G01N 21/7703* (2013.01); *G01N 21/80* (2013.01); *G01N 2021/7786* (2013.01)

(58) Field of Classification Search
CPC ......... A61B 5/686; A61B 5/0075; A61B 5/01; A61B 5/14539; G01K 11/32; G01N 21/80; G01N 21/7703; G01N 2201/088; G01N 2021/7786
See application file for complete search history.

(56) References Cited

U.S. PATENT DOCUMENTS

| | | | |
|---|---|---|---|
| 5,115,811 A | 5/1992 | Hartlaub et al. | |
| 5,280,548 A | 1/1994 | Atwater et al. | |
| 10,105,080 B1 * | 10/2018 | Kam | A61B 5/14514 |
| 2008/0275659 A1 * | 11/2008 | Miller | G01N 21/33 702/84 |

(Continued)

OTHER PUBLICATIONS

Yang, X.H., et al., "Fluorescence pH probe based on microstructured polymer optical fiber", Optics Express, 2007, p. 16478-16483, vol. 15 No. 25.

(Continued)

*Primary Examiner* — Sang H Nguyen
(74) *Attorney, Agent, or Firm* — Office of Chief Counsel for National Institute of Standards and Technology

(57) ABSTRACT

A pH photothermal spectrometer includes a container that receives an analyte medium and pH-sensitive chromophore. An excitation fiber and optical thermometer are disposed in the container. The optical thermometer include a light receiver disposed on a temperature detector fiber.

20 Claims, 13 Drawing Sheets

(56) References Cited

U.S. PATENT DOCUMENTS

| | | | |
|---|---|---|---|
| 2012/0075619 A1* | 3/2012 | Nieman | G01N 21/474 356/73 |
| 2015/0297086 A1* | 10/2015 | Hong | G01N 21/6456 600/431 |
| 2018/0274988 A1* | 9/2018 | Sabri | G01K 11/20 |
| 2019/0128894 A1* | 5/2019 | Jain | C23C 16/403 |
| 2019/0223795 A1* | 7/2019 | Patolsky | A61B 5/14532 |

OTHER PUBLICATIONS

Netto, E.J., et al., "A fiber-optic broad-range pH sensor system for gastric measurements", Sensors and Actuators B, 1995, p. 157-163, vol. 29.

Gaur, S.S., et al., "Synthesis and Analysis of Planar Optical Waveguides as pH Sensors", Recent Innovations in Chemical Engineering, 2018, p. 40-44, vol. 11.

Hartings, M.R., et al., "A photonic pH sensor based on photothermal spectroscopy", Sensors and Actuators B: Chemical, 2019, p. 127076, vol. 301.

Rovati, L., et al., "Plastic Optical Fiber pH Sensor Using a Sol-Gel Sensing Matrix", Fiber Optic Sensors, 2012, p. 415-438, DOI: 10.5772/26517.

* cited by examiner

PH PHOTOTHERMAL SPECTROMETER AND PERFORMING PH PHOTOTHERMAL SPECTROSCOPY

CROSS REFERENCE TO RELATED APPLICATIONS

The application claims priority to U.S. Provisional Patent Application Ser. No. 63/084,313 filed Sep. 28, 2020, the disclosure of which is incorporated herein by reference in its entirety.

STATEMENT REGARDING FEDERALLY SPONSORED RESEARCH

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, Md., 20899; voice (301) 301-975-2573; email tpo@nist.gov; reference NIST Docket Number 19-051US1.

BRIEF DESCRIPTION

Disclosed is a pH photothermal spectrometer for performing pH photothermal spectroscopy, the pH photothermal spectrometer comprising a container comprising an interior bounded by a wall of the container, such that the container receives an analyte medium and a pH-sensitive chromophore, the pH-sensitive chromophore comprises an optical absorption spectrum that adjusts to a pH of the analyte medium, the analyte medium comprising a analyte temperature TA; and optionally receives a fiber encapsulation matrix in which are disposed the analyte medium and the pH-sensitive chromophore; an excitation fiber disposed in the container in optical communication with the pH-sensitive chromophore and that receives a first excitation light comprising a first wavelength and a second excitation light comprising a second wavelength; and communicates the first excitation light and the second excitation light to the pH-sensitive chromophore, such that the pH-sensitive chromophore receives the first excitation light and the second excitation light; and absorbs a first amount A1 of the first excitation light and a second amount A2 of the second excitation light based on the pH of the analyte medium such that absorption of the first excitation light or the second excitation light increases the analyte temperature TA of the analyte medium; and an optical thermometer disposed in the container and comprising a temperature detector fiber that receives a probe light comprising a probe light wavelength in a first optical amount O1; and receives a reflected light comprising the probe light wavelength from a light receiver; and a light receiver disposed on a terminus of the temperature detector fiber in optical communication with the temperature detector fiber and in thermal communication with the analyte medium; and comprising a receiver temperature TR that adjusts to match the analyte temperature TA; and an optical resonance OR at a resonance wavelength LR that changes in response to a change in the receiver temperature TR, such that the light receiver receives the probe light from the temperature detector fiber; produces, from the probe light, a reflected light in a second optical amount O2 and comprising the probe light wavelength, such that the second optical amount O2 of the reflected light depends on the receiver temperature TR of the light receiver, so that a ratio of the first optical amount O1 to the second optical amount O2 provides a pH of the analyte medium; and communicates the reflected light to the temperature detector fiber; and the temperature detector fiber receives the reflected light from the light receiver.

Disclosed is a process for performing pH photothermal spectroscopy with a pH photothermal spectrometer, the process comprising receiving, by the excitation fiber, the first excitation light that comprises the first wavelength and the second excitation light that comprises the second wavelength; contacting the pH-sensitive chromophore with the analyte medium; adjusting the optical absorption spectrum of the pH-sensitive chromophore in response to the pH of the analyte medium; communicating the first excitation light and the second excitation light from the excitation fiber to the pH-sensitive chromophore; receiving, by the pH-sensitive chromophore, the first excitation light and the second excitation light; absorbing, by the pH-sensitive chromophore, the first amount A1 of the first excitation light based on the pH of the analyte medium; absorbing, by the pH-sensitive chromophore, the second amount A2 of the second excitation light based on pH of the analyte medium; adjusting the analyte temperature TA of the analyte medium in response to the pH-sensitive chromophore absorbing the first excitation light and the second excitation light; adjusting the receiver temperature TR of the light receiver to match the analyte temperature TA of the analyte medium in response to adjusting the analyte temperature TA of the analyte medium; receiving, by the light receiver, the probe light in the first optical amount O1 from the temperature detector fiber; producing, by the light receiver from the probe light, the reflected light in the second optical amount O2 that depends on the receiver temperature TR of the light receiver, the reflected light comprising the probe light wavelength; and determining the pH of the analyte medium from a ratio of the first optical amount O1 to the second optical amount O2 to perform pH photothermal spectroscopy.

BRIEF DESCRIPTION OF THE DRAWINGS

The following description should not be considered limiting in any way. With reference to the accompanying drawings, like elements are numbered alike.

DETAILED DESCRIPTION

A detailed description of one or more embodiments is presented herein by way of exemplification and not limitation.

It has been discovered that a pH photothermal spectrometer probes a pH-dependent change in absorbance of a pH-sensitive chromophore in response to irradiation thereof by different wavelengths of light to determine a difference in temperature rise due to differences in light absorbance of the pH-sensitive chromophore at the different wavelengths of light. An absorption profile of the pH-dependent absorption of light of the pH-sensitive chromophore governs an amount of light absorbed at a particular wavelength. Light absorbed by the pH-sensitive chromophore is thermalized in an analyte matrix that includes the pH-sensitive chromophore so that as a temperature of the analyte matrix changes, the temperature change of the analyte matrix is detected by an optical thermometer disposed in the analyte matrix.

Here, the pH photothermal spectrometer measures pH and can be used, e.g., in bio-industrial processing, tissue engineering industry, and the like that involve a small footprint probe that is compatible with a biological environment, wherein the pH photothermal spectrometer does not interfere with cell growth, operates in a high ionic strength solution environment, can be embedded in a substrate to measure pH via access to an optically dark area, is disposable, or is stable over a lengthy period without weekly re-calibration.

The pH photothermal spectrometer can include optical waveguides to deliver light and detect temperature change so that the pH photothermal spectrometer can be disposed in a biocompatible matrix, e.g., in a region that is inaccessible to optical microscopy. Furthermore, the pH photothermal spectrometer can include soft, biocompatible materials that match a mechanical or chemical environment for cellular or tissue growth without biofouling the pH photothermal spectrometer. In the pH photothermal spectrometer, the pH-sensitive chromophore can be covalently attached to a proton-permeable waveguide for optical or photothermal spectroscopy for measurement of pH. Advantageously, photo-thermal spectroscopy to measure pH, as compared with a volumetric change, in a hydrogel that is probed by changes in a bandgap resonance wavelength can be performed in an ionic solution. In this manner, the pH photothermal spectrometer overcomes technical limitations of conventional polymeric waveguide sensors that operate at low ionic strengths but not high ionic strength because such conventional waveguide sensor infer pH from effects of osmotic pressure-induced swelling of a hydrogel. Beneficially, the pH photothermal spectrometer operates without undergoing a significant hysteresis upon dehydration to eliminate device failure that occurs in some conventional electrical pH devices.

Figure 9:
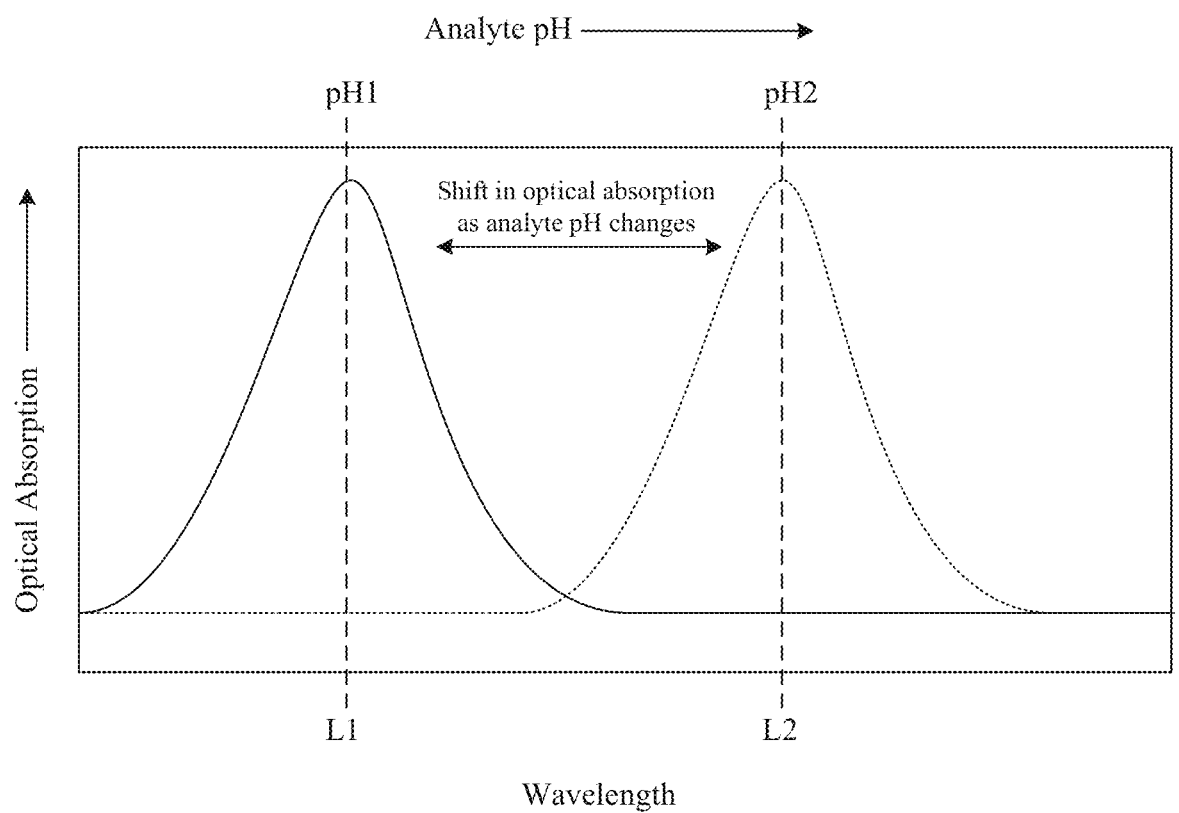
FIG. 9 shows an optical absorption spectrum of a pH-sensitive chromophore as a graph of optical absorption versus wavelength.
Figure 10:
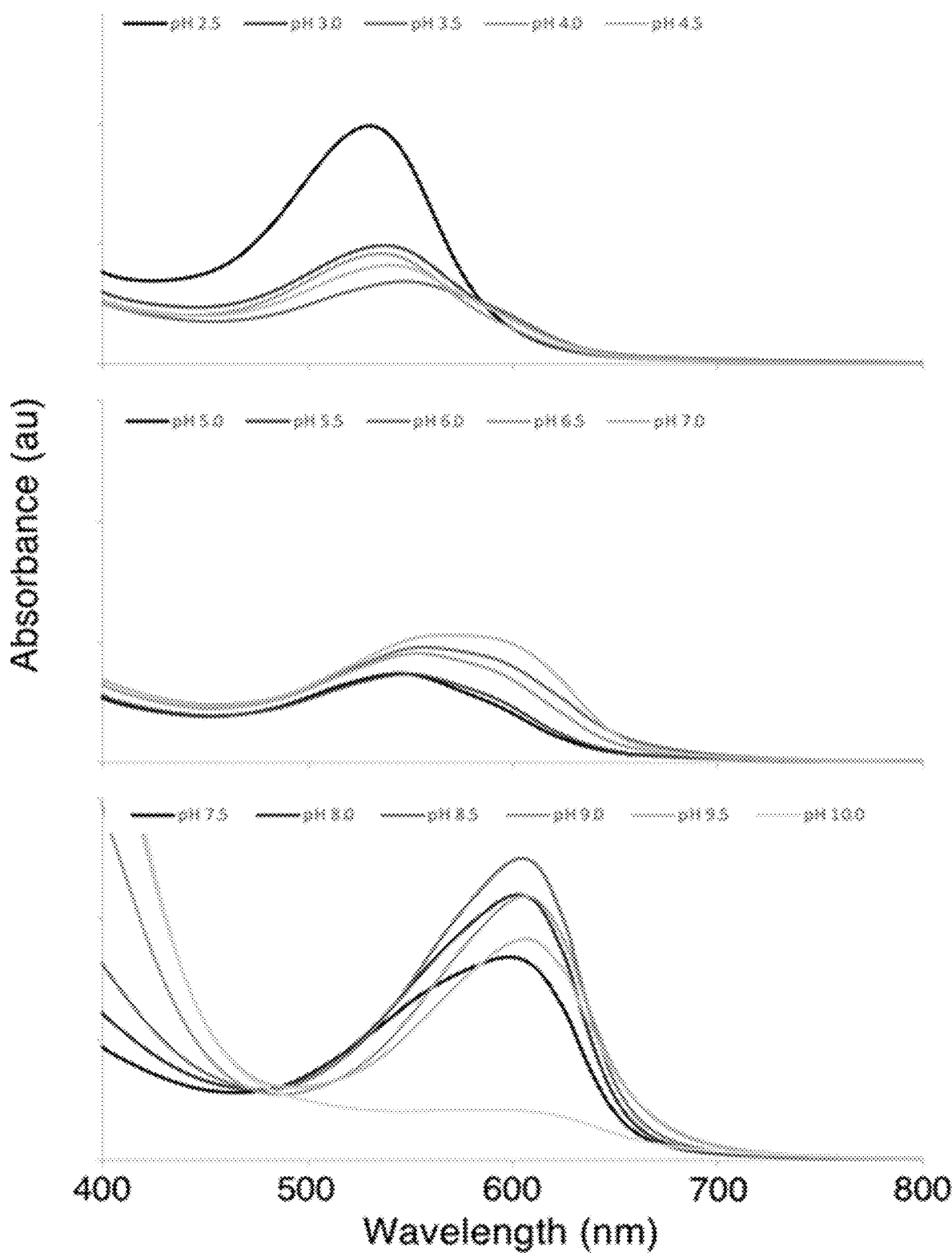
FIG. 10 shows a graph of absorbance versus wavelength for UV-visible absorbance of red cabbage extract for pH of 2.5, 3.0, 3.5, 4.0, 4.5, 5.0, 5.5, 6.0, 6.5, 7.0, 7.5, 8.0, 8.5, 9.0, 9.5, and 10.0.

It should be appreciated that pH photothermal spectrometer 200 performs pH photothermal spectroscopy to determine pH of analyte medium 204 via a thermal response of optical thermometer 216 to light absorption of pH-sensitive chromophore 206 disposed among analyte medium 204. In an embodiment, with reference to FIG. 1, FIG. 2, FIG. 3, FIG. 4, and FIG. 5, pH photothermal spectrometer 200 includes: container 201 including interior 202 bounded by wall 220 of container 201, such that container 201 receives analyte medium 204 and pH-sensitive chromophore 206, pH-sensitive chromophore 206 includes optical absorption spectrum (e.g., as shown in FIG. 9 or FIG. 10) that adjusts to a pH of analyte medium 204, analyte medium 204 including analyte temperature TA; and optionally receives fiber encapsulation matrix 203 in which are disposed analyte medium 204 and pH-sensitive chromophore 206; excitation fiber 207 disposed in container 201 in optical communication with pH-sensitive chromophore 206 and that receives first excitation light 208 including first wavelength 209 and second excitation light 210 including second wavelength 211; and communicates first excitation light 208 and second excitation light 210 to pH-sensitive chromophore 206, such that pH-sensitive chromophore 206 receives first excitation light 208 and second excitation light 210; and absorbs first amount A1 of first excitation light 208 and second amount A2 of second excitation light 210 based on the pH of analyte medium 204 such that absorption of first excitation light 208 or second excitation light 210 increases analyte temperature TA of analyte medium 204; and optical thermometer 216 disposed in container 201 and including temperature detector fiber 205 that receives probe light 217 including probe light wavelength 224 in first optical amount O1; and receives reflected light 218 including probe light wavelength 224 from light receiver 214; and light receiver 214 disposed on terminus of temperature detector fiber 205 in optical communication with temperature detector fiber 205 and in thermal communication with analyte medium 204; and including receiver temperature TR that adjusts to match analyte temperature TA; and optical resonance OR at resonance wavelength LR that changes in response to a change in receiver temperature TR, such that light receiver 214 receives probe light 217 from temperature detector fiber 205; produces, from probe light 217, reflected light 218 in second optical amount O2 and including probe light wavelength 224, such that second optical amount O2 of reflected light 218 depends on receiver temperature TR of light receiver 214, so that a ratio of first optical amount O1 to second optical amount O2 provides the pH of analyte medium 204; and communicates reflected light 218 to temperature detector fiber 205; and temperature detector fiber 205 receives reflected light 218 from light receiver 214.

Container 201 can be a plate well or other structure that can contain fluids such as cell media or a composition with a range of viscosity from very fluidic to highly viscous. Plate wells are typically arranged in an array format for disposal of multiple different samples for independent testing. A volume of container 201 is sufficient to hold fiber encapsulation matrix 203, analyte medium 204, pH-sensitive chromophore 206, light receiver 214, temperature detector fiber 205, and excitation fiber 207 in interior 202 that is bounded by wall 220. Accordingly, the volume of container 201 can be from 10 nanoliters to $10^6$ liters, specifically from 100 nanoliters to 10 centiliters, and more specifically from 1 microliter to 100 microliters.

Temperature detector fiber 205 and excitation fiber 207 independently are optical fibers that communicate light (e.g., 208, 210, 217, 218) into or out of excitation fiber 207, particularly sensing volume 215, wherein first excitation light 208 and second excitation light 210 communicate from excitation fiber 207 and spread into light cone 213 and interact with analyte medium 204 proximate to light receiver 214. Excitation fiber 207 can be an optical fiber that propagates ultraviolet or visible light as first excitation light 208 or second excitation light 210 that can have respectively first wavelength 209 and second wavelength 211, e.g., from 200 nanometers (nm) to 1200 nm, specifically from 300 nm to 1000 nm, and more specifically from 400 nm to 900 nm. Temperature detector fiber 205 can be an optical fiber that propagates infrared light as probe light 217 or reflected light 218 that can have probe light wavelength 224, e.g., from 1000 nanometers (nm) to 6000 nm, specifically from 1100 nm to 4000 nm, and more specifically from 1100 millimeters to 2500 nm.

Light receiver 214 can be a fiber Bragg grating (FBG), on-chip thermometer, fiber optic thermometer (e.g., Raman or Brillouin), or a florescent particle coupled to temperature detector fiber 205, e.g., nitrogen vacancy (NV) diamond. It should be appreciated that light receiver 214 receives probe light 217 in first optical amount O1 from temperature detector fiber 205 and reflects probe light 217 as reflected light 218 in second optical amount O2. Second optical amount of 2 depends on receiver temperature TR of optical receiver 214 because resonance wavelength LR at which light receiver 214 reflect probe light 217 as reflected light 218 changes as a function of receiver temperature TR. Moreover, light receiver 214 in combination with temperature detector fiber 205 make up optical thermometer 216. Exemplary optical thermometer 216 is described in U.S. patent application Ser. No. 16/589,793, which is incorporated by reference in its entirety.

Fiber port 212 can be disposed on container 201 for disposal of optical thermometer 216 or excitation fiber 207 through and in container 201. Fiber port can include a grommet, sleeve, or pigtail for continuous, non-interrupted optical communication of light (e.g., first excitation light 208, second excitation light 210, probe light 217, reflected light 218) through excitation fiber 207 or temperature detector fiber 205.

Fiber encapsulation matrix 203 can be disposed in container 201 to encapsulate light receiver 214, excitation fiber 207, or a combination thereof to maintain a relative position in interior 202. Fiber encapsulation matrix 203 can be a gel such as a hydrogel or other sol-gel composite. It is contemplated that fiber encapsulation matrix 203 is permeable to fluid flow or disposal of analyte medium 204 and pH-sensitive chromophore 206 therein. Fiber encapsulation matrix 203 is thermally conductive to equilibrate the temperature of light receiver rapidly thermally 214 to analyte medium 204 in which is disposed pH-sensitive chromophore 206. Further, fiber encapsulation matrix 203 provides rapid contact between pH-sensitive chromophore 206 and analyte medium 204 so that pH-sensitive chromophore 206 is subject to the pH of analyte medium 204.

Analyte medium 204 is a fluid that a has a pH to which pH-sensitive chromophore 206 is sensitive so that the absorption spectrum of pH-sensitive chromophore 206 changes due to the pH of analyte medium 204 as shown in FIG. 9 and FIG. 10. Analyte medium 204 can provide a pH that is from 1 to 15, specifically from 2 to 12, and more specifically from 5 to 8. It is contemplated analyte medium 204 can be single moiety or can include multiple moieties that can include a solvent, organic compound, inorganic, carbohydrate, cellular component (e.g., mitochondria and the like), a biological sample such as a cell (e.g., prokaryote or eukaryote) that can be an animal cell or plant cell, and the like. In an embodiment, analyte medium 204 is human blood that includes typical components of human blood, wherein the human blood can be synthetic or naturally occurring or from a healthy or diseased human.

In an embodiment, pH-sensitive chromophore 206 can be subject to diffusion in analyte medium 204; disposed in the fiber encapsulation matrix 203 via entropic trapping, covalent bond attachment, or electrostatic trapping; and the like. Exemplary pH-sensitive chromophore 206 includes an acid-base indicator (e.g., phenol red, cabbage extract, and the like) that can be compatible with biological samples or incompatible with biological samples. A color change (i.e., a change of the optical absorption spectrum by shifting a maximum of absorbance in the spectrum) of pH-sensitive chromophore 206 can occur at a selected pH such as around an acidic pH, around a neutral pH, or around a basic pH, wherein the color change can occur over a broad pH range (e.g., more than 1 pH units such as 2, 3, or 4 pH units) or narrow pH range (e.g., 0.25 to 1 pH unit).

Figure 1:
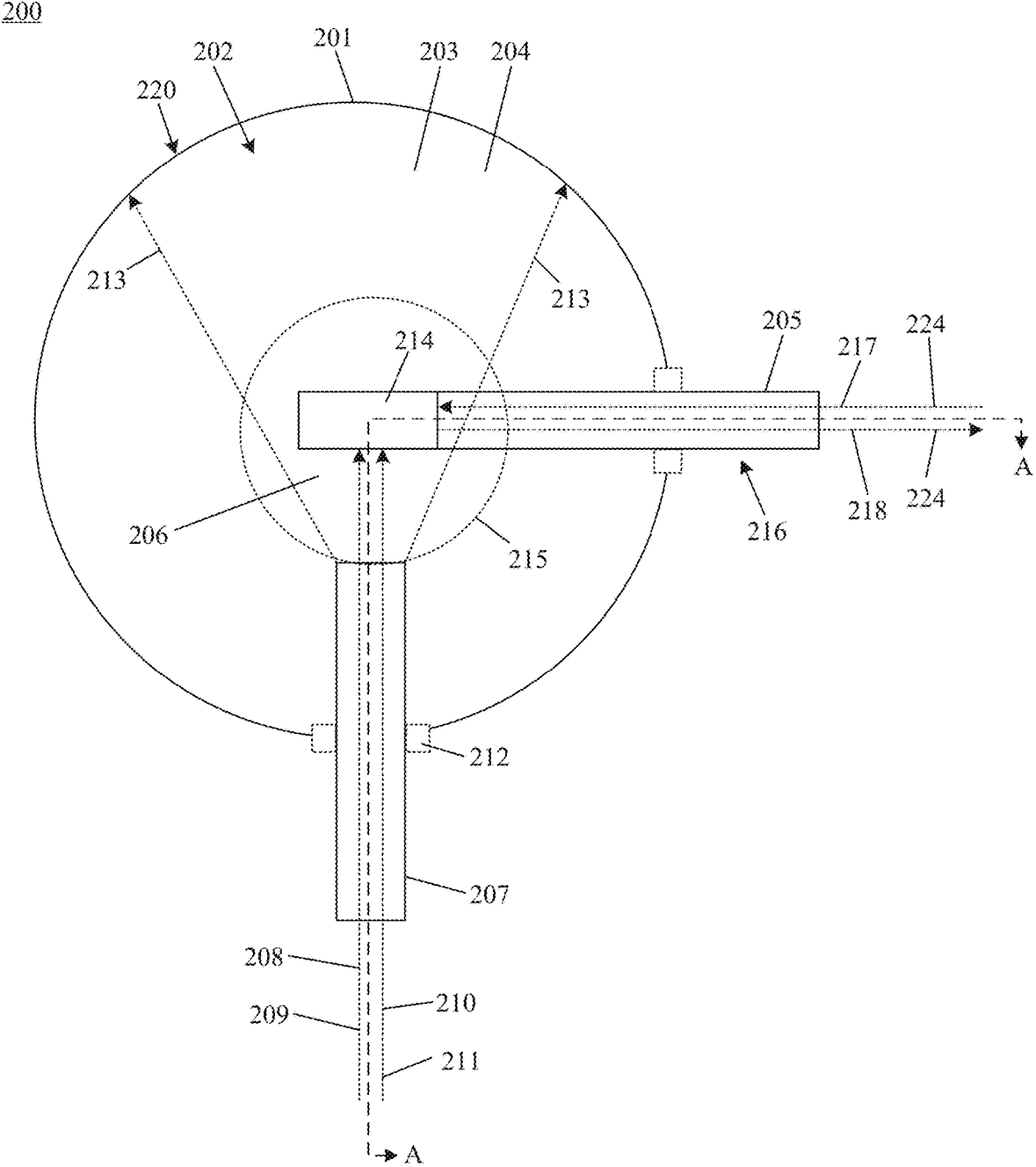
FIG. 1 shows a pH photothermal spectrometer.
Figure 2:
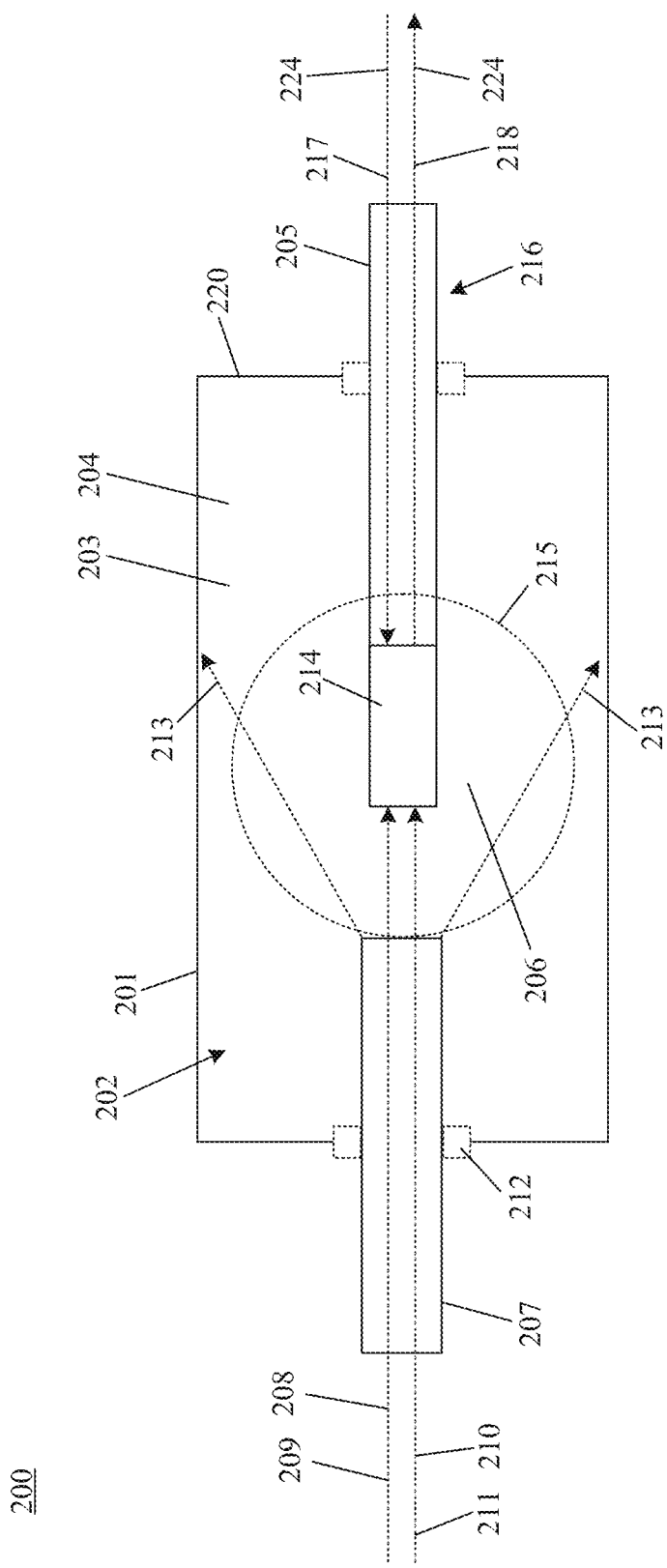
FIG. 2 shows a cross-section along line A-A of the pH photothermal spectrometer shown in FIG. 1.
Figure 3:
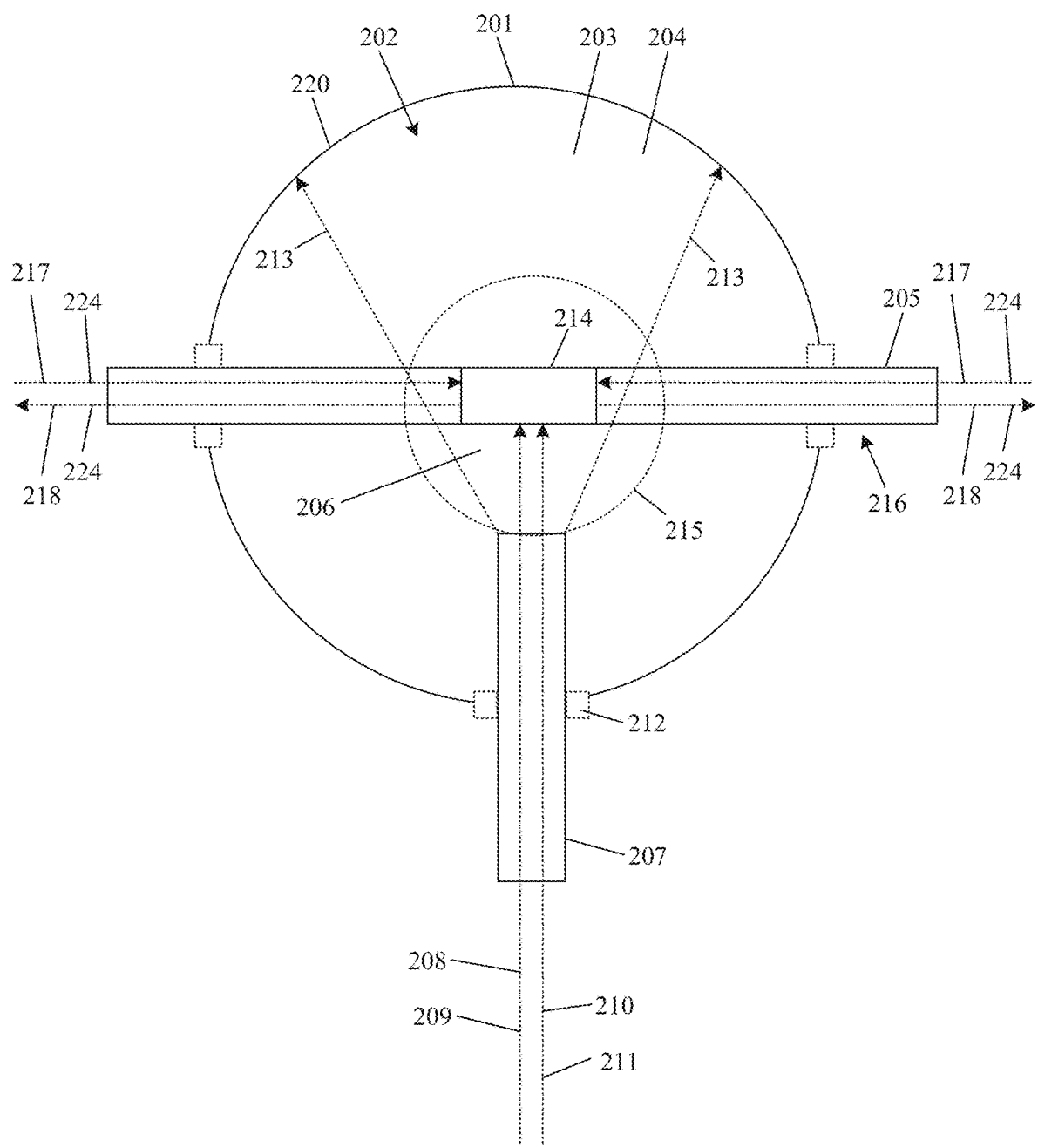
FIG. 3 shows a pH photothermal spectrometer.
Figure 4:
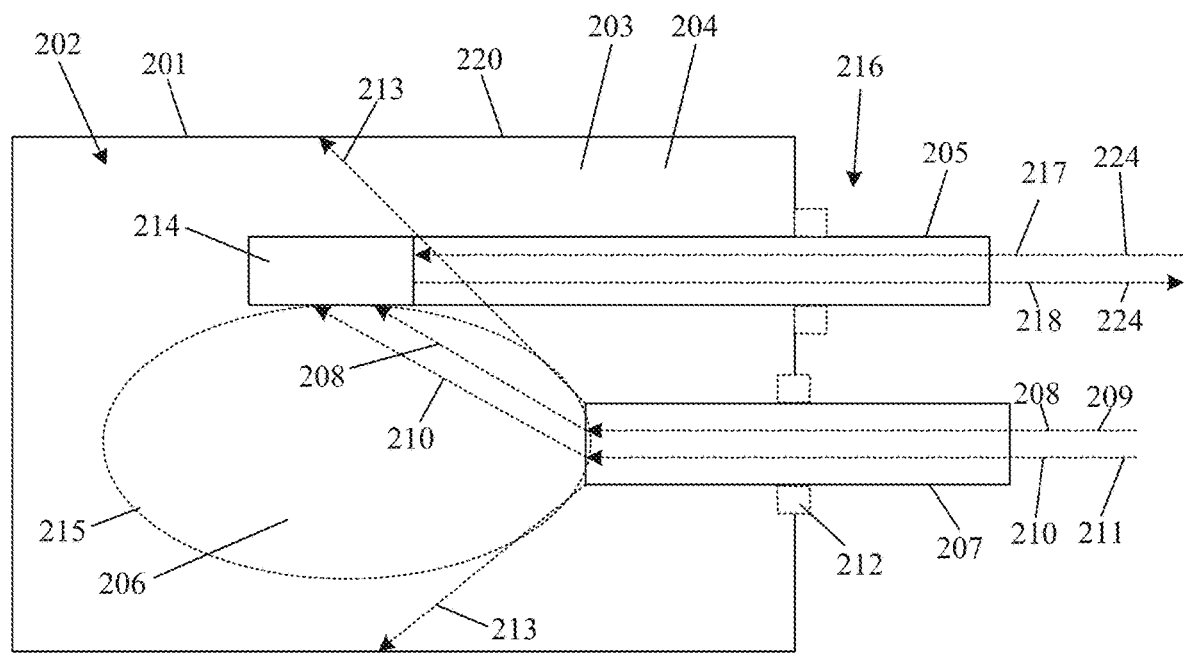
FIG. 4 shows a pH photothermal spectrometer.
Figure 5:
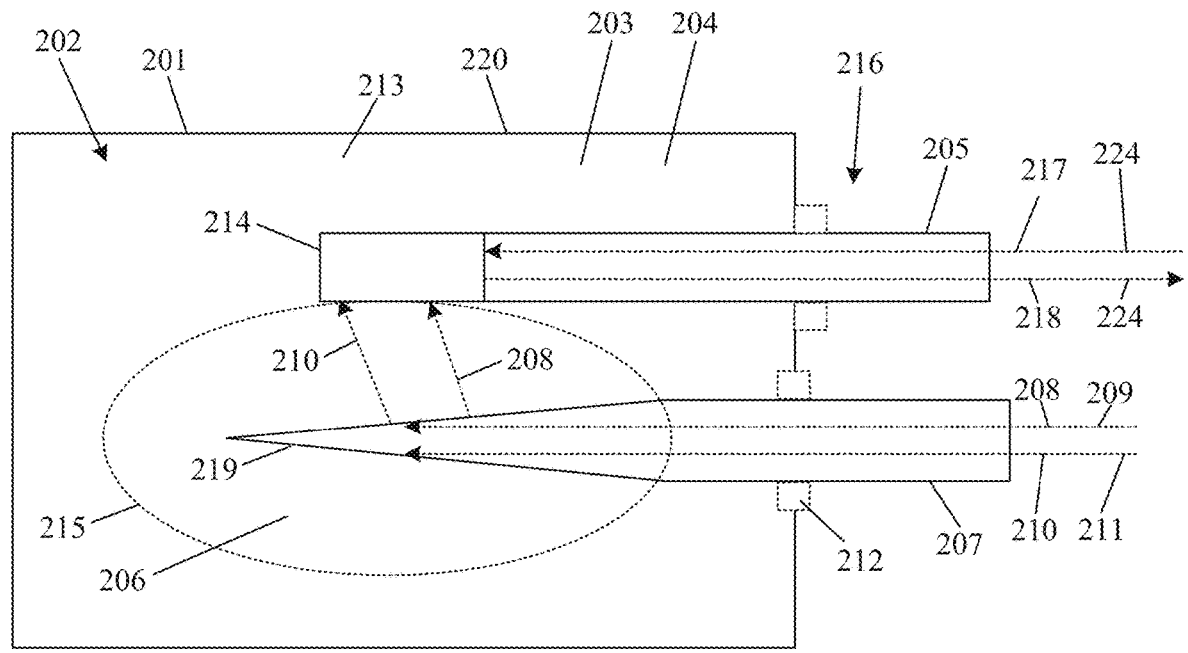
FIG. 5 shows a pH photothermal spectrometer.

A configuration of optical thermometer 216 relative to excitation fiber 207 can be selected to accord to a particular use of pH photothermal spectrometer 200, e.g., as an implant in biological tissue (e.g., human muscle tissue) to monitor a biological condition (e.g., acidosis) or presence or amount of a compound (e.g., a therapeutic drug) is such biological tissue. In an embodiment, with reference to FIG. 1, optical thermometer 216 can be disposed at an orthogonal or obtuse angle to excitation fiber 207 such that optical thermometer 216 terminates in interior 202 of container 201. In an embodiment, with reference to FIG. 3, optical thermometer 216 can be disposed at an orthogonal or obtuse angle to excitation fiber 207 such that optical thermometer 216 dually extends into interior 202 of container 201 from two ports of container 201. In an embodiment, with reference to FIG. 4, optical thermometer 216 can be disposed parallel to excitation fiber 207 in container 201. According to an embodiment, with reference to FIG. 4 and FIG. 5, excitation fiber 207 can terminate as a straight fiber section proximate to light receiver 214 as shown in FIG. 4 or can terminate in optical taper 219 proximate to light receiver 214 as shown in FIG. 5.

Figure 8:
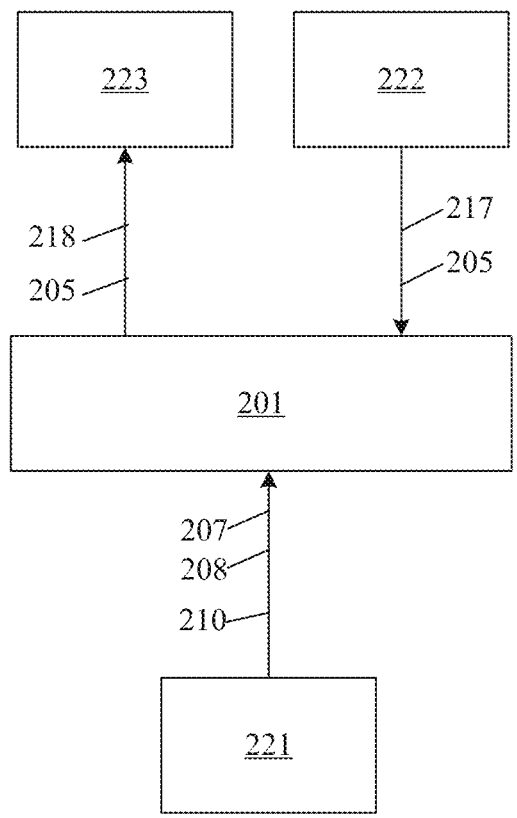
FIG. 8 shows a pH photothermal spectrometer.

In an embodiment, with reference to FIG. 8, pH photothermal spectrometer 200 includes excitation light source 221 in optical communication with excitation fiber 207, wherein excitation light source 221 provides first excitation light 208 and second excitation light 210 to excitation fiber 207. Excitation light source 221 can be a laser or set of lasers that provides arbitrary wavelengths of light according to desired wavelengths for first wavelength 209 and second wavelength 211. Probe light source 222 can be in optical communication with temperature detector fiber 205 to provide probe light 217 to temperature detector fiber 205. Probe light source 222 can be a laser that provides an arbitrary wavelength of light according to desired wavelength for probe light 217. Detector 223 can be in optical communication with temperature detector fiber 205 to receive reflected light 218 from optical thermometer 216. An exemplary detector 223 includes a photodiode or power meter.

In an embodiment 200 includes a signal generator (XYZ) that produces an excitation signal, e.g., a square wave pulse that may be used to control 221 such as to produce a sequence of pulses of first excitation light 208 and first wavelength 209 of time period T, wherein T can be from 1 femtosecond to 1000 seconds, specifically 1 nanoseconds to 300 seconds, and more specifically 1 microsecond to 100 second. An optical splitter, in communication with excitation light source 221 and excitation fiber 207 can deliver first excitation light 208 and first wavelength 209 to a light receiver, e.g., a photodiode or power meter, for ratiometric measurement of optical power of first excitation light 208 and first wavelength 209. In addition, a signal generator (XYY), in communication with probe light source 222, that produces a periodic signal such as a sine wave or a triangular wave, can sweep the probe wavelength of probe light source 222 for measurement of resonance wavelength of light receiver 214. A lock-in amplifier and laser locking circuit in communication with detector 223 provides locking of probe light source 222 to light receiver 214 for automatic selection of probe light 217. In addition, an optical splitter in communication with temperature detector fiber 205 and probe light source 222 can deliver probe light 217 to wavelength reference that can be, e.g., a wavemeter, frequency comb, or gas wavelength reference cell. An optical circulator in communication with temperature detector fiber 205 and probe light source 222 can separate reflected light 218 from probe light 217 and communicate reflected light 218 to detector 223.

It should be appreciated that pH photothermal spectrometer 200 can be made in various ways. In an embodiment, a process for making pH photothermal spectrometer 200 includes: providing container 201; forming a first port in wall 220 to receive excitation fiber 207; disposing excitation fiber 207 in interior 202 through the first port; forming a second port in wall 220 to receive optical thermometer 216; disposing optical thermometer 216 in interior 202 through the second port; disposing fiber encapsulation matrix 203 in interior 202 to fixedly maintain a position of light receiver 214 and temperature detector fiber 205 in interior 202 to make pH photothermal spectrometer 200.

The process for making pH photothermal spectrometer 200 also can include parallel arrangement of temperature detector fiber 205 and excitation fiber 207 with fiber encapsulation matrix that fix the relative position of the two fibers. Excitation fiber 207 can have an adiabatic taper by the application of constant tension under a heat source. The adiabatic tapers allow the excitation light first excitation light 208 and first wavelength 209 to gradually exit excitation fiber 207 over the tapered area allowing second excitation light 210 and second wavelength 211 to interact with the chromophore interposed between temperature detector fiber 205 and excitation fiber 207. The fiber matrix can be formed using photo polymerization or thermal setting of polymers such as polyethylene.

It should be appreciated that pH photothermal spectrometer 200 can be made in various ways. In an embodiment, a process for making pH photothermal spectrometer 200 includes: providing container 201; forming a first port in wall 220 to receive excitation fiber 207; disposing excitation fiber 207 in interior 202 through the first port; forming a second port in wall 220 to receive optical thermometer 216; disposing optical thermometer 216 in interior 202 through the second port, disposing fiber encapsulation matrix 203 in interior 202 to fixedly maintain a position of light receiver 214 and temperature detector fiber 205 in interior 202 to make pH photothermal spectrometer 200.

The process for making pH photothermal spectrometer 200 also can include parallel arrangement of temperature detector fiber 205 and excitation fiber 207 with fiber encapsulation matrix being used fix the relative position of the two fibers. Excitation fiber 207 may have an adiabatic taper by the application of constant tension under a heat source. The adiabatic tapers allow the excitation light first excitation light 208 and first wavelength 209 to gradually exit excitation fiber 207 over the tapered area allowing the excitation wavelength second excitation light 210 and second wavelength 211 to interact with the chromophore interposed between temperature detector fiber 205 and excitation fiber 207. The fiber matrix may be formed using photo polymerization or thermal setting of polymers such as polyethylene glycol or poly-vinyl alcohol.

Disclosed is a process for performing pH photothermal spectroscopy with pH photothermal spectrometer 200, the process including: receiving, by excitation fiber 207, first excitation light 208 that includes first wavelength 209 and second excitation light 210 that includes second wavelength 211; contacting pH-sensitive chromophore 206 with analyte medium 204; adjusting optical absorption spectrum of pH-sensitive chromophore 206 in response to the pH of analyte medium 204; communicating first excitation light 208 and second excitation light 210 from excitation fiber 207 to pH-sensitive chromophore 206; receiving, by pH-sensitive chromophore 206, first excitation light 208 and second excitation light 210; absorbing, by pH-sensitive chromophore 206, first amount A1 of first excitation light 208 based on the pH of analyte medium 204; absorbing, by pH-sensitive chromophore 206, second amount A2 of second excitation light 210 based on pH of analyte medium 204, adjusting analyte temperature TA of analyte medium 204 in response to pH-sensitive chromophore 206 absorbing first excitation light 208 and second excitation light 210 through thermal equilibration of analyte medium 204 to the temperature of pH-sensitive chromophore 206; adjusting receiver temperature TR of light receiver 214 to match analyte temperature TA of analyte medium 204 in response to adjusting analyte temperature TA of analyte medium 204 through heat transfer between analyte medium 204 and light receiver 214; receiving, by light receiver 214, probe light 217 in first optical amount O1 from temperature detector fiber 205; producing, by light receiver 214 from probe light 217, reflected light 218 in second optical amount O2 that depends on receiver temperature TR of light receiver 214, reflected light 218 including probe light wavelength 224; and determining the pH of analyte medium 204 from a ratio of first optical amount O1 to second optical amount O2 to perform pH photothermal spectroscopy.

Determining the pH of analyte medium 204 from the ratio of first optical amount O1 to second optical amount O2 (RATIO) includes constructing a calibration model of using linear regression where the RATIO is the dependent variable and pH the independent variable. To train the model, measurement of RATIO are obtained by introducing aqueous solution of known pH values to pH photothermal spectrometer 200. The measured RATIO values and corresponding pH values are used as input to the regression model to calculate a linear relationship between RATIO and pH. To measure the pH of analyte medium 204 whose pH may not be known prior to measurement, RATIO is measured using pH photothermal spectrometer 200 following which the RATIO is used as input variable in calibration model to solve for pH.

In an embodiment, the process for performing pH photothermal spectroscopy further includes communicating, from light receiver 214, reflected light 218 to temperature detector fiber 205; and receiving, by temperature detector fiber 205, reflected light 218 from the light receiver 214. Here, detector 223 can receive reflected light 218 to obtain second optical amount O2 of reflected light 218 from which the pH of analyte medium 204 can be determined.

In an embodiment, the process for performing pH photothermal spectroscopy further includes calibrating pH photothermal spectrometer 200 by measuring the ratio of probe wavelengths 218 before after excitation light 208 and 209 are exposed to the chromophore (call it RATIO2). This measurement provides the relative increase in temperature due to absorption of excitation light 208 and 209 and is equivalent to RATIO. To achieve a higher accuracy, the RATIO2 maybe multiplied by the ratio of optical power of excitation light 208 and 209. Taking the ratio of reflected light 218 before and after excitation with excitation light 208 and 209 removes step of calibrating the temperature to frequency response of light receiver 214. Scaling this response factor by the ratio of excitation light 208 and 209 corrects drift in power of the excitation light and removes a source of error in pH measurement. In this manner, the scaled RATIO2 pH photothermal spectrometer 200 can be used to provide the pH of analyte medium 204 by constructing a calibration model of using linear regression where the RATIO2 is the dependent variable and pH the independent variable. To train the model, measurement of RATIO2 are obtained by introducing aqueous solution of known pH values to pH photothermal spectrometer 200. The measured RATIO2 values and corresponding pH values are input to the regression model to calculate a linear relationship between RATIO2 and pH. To measure the pH of analyte medium 204 whose pH may not be known prior to measurement, RATIO2 is measured using 200 following which the RATIO2 is used as input variable in calibration model to solve for pH.

It should be appreciated that pH photothermal spectrometer 200 and processes disclosed herein have numerous beneficial uses including a small form factor and biocompatibility of constituent components. Advantageously, pH photothermal spectrometer 200 overcomes limitations of technical deficiencies of conventional devices such as temperature dependence by employing ratiometric measurements. Further, pH photothermal spectrometer 200 does not require excitation light 208 and 209 to be measured after interaction with chromophore removing a technical barrier to the use of optical pH sensors where losses in optical power of excitation light 208 and 209 are a source of measurement error.

Beneficially, pH photothermal spectrometer 200 does not use toxic materials such as metals, corrosive salts or toxic dyes. Moreover, pH photothermal spectrometer 200 and processes herein unexpectedly provide a low drift measurement where the device does not need to be recalibrated over a period of 2-3 weeks. Conventional devices require recalibration daily to provide accurate pH measurement. As such, pH photothermal spectrometer 200, decontaminated and calibrated, can be embedded into an analyte, e.g., a microtissue or biomanufacturing vessel, and used over the course of cell proliferation, differentiation and activity cycle without loss of measurement accuracy. The ability to embed pH photothermal spectrometer 200 for duration of cell life eliminates a potential route through which deleterious infection could be introduced.

The articles and processes herein are illustrated further by the following Examples, which are non-limiting.

EXAMPLES

Example 1. Photothermal Detection of pH

Figure 6:
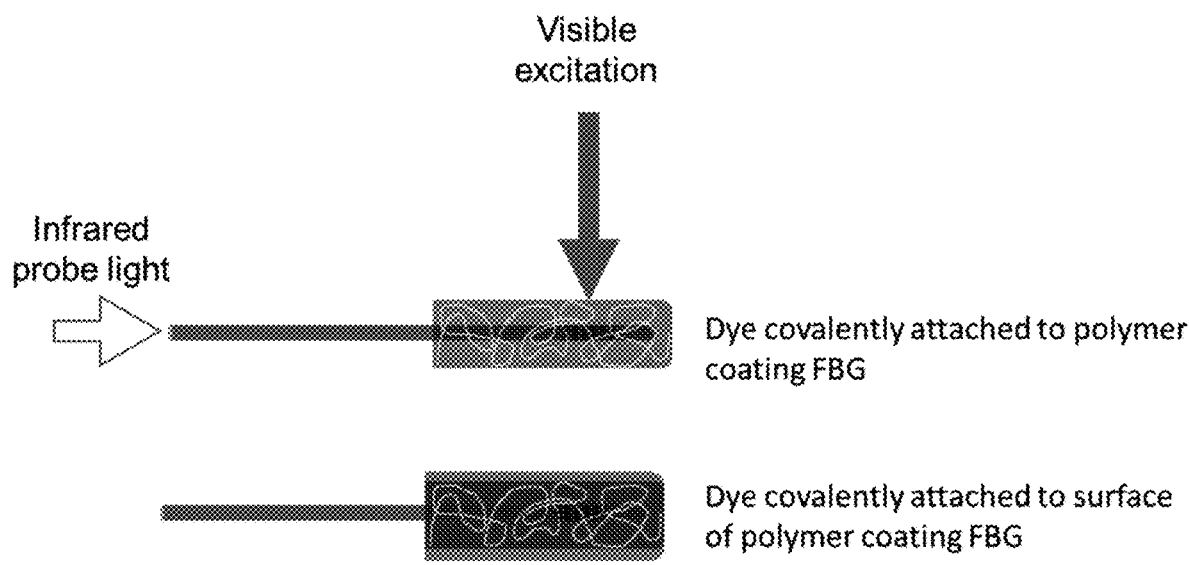
FIG. 6 shows pH photothermal spectroscopy.

Here, a pH photothermal spectrometer measured a local pH over a small volume that was contained in an intersection of a light cone and a light receiver over several days without recalibration, wherein data is shown in FIG. 6.

Example 2. Photothermal Detection of pH

Figure 7:
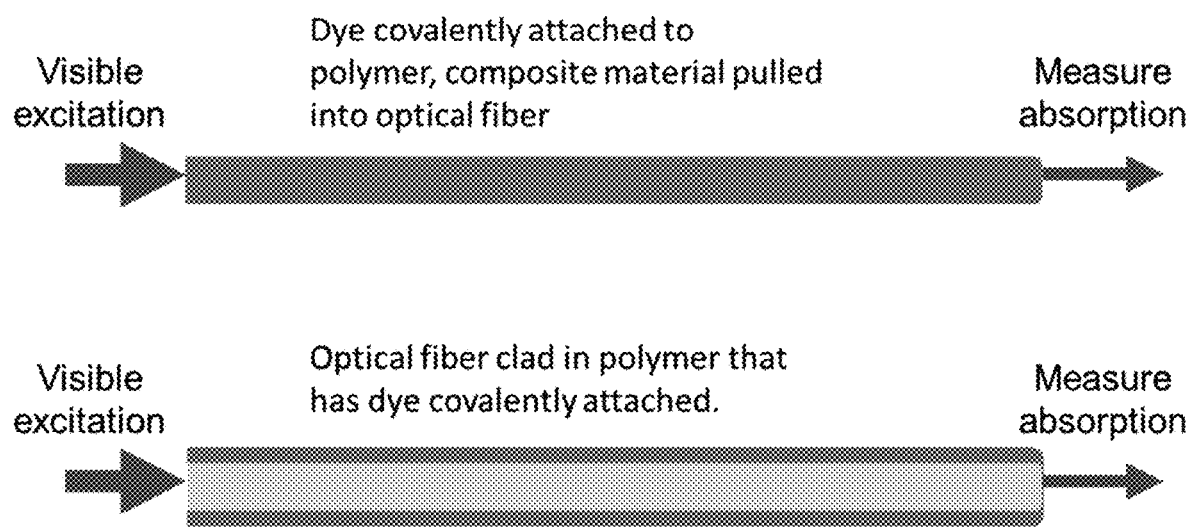
FIG. 7 shows pH photothermal spectroscopy.

An excitation optical fiber with embedded chromophore measured changes in the absorption spectra of a chromophore due to changes in pH of the analyte, wherein data is shown in FIG. 7.

Example 3. Photonic pH Sensor Based on Photothermal Spectroscopy

Three-dimensional tissue analogues and cell-laden constructs composed of synthetic or biopolymeric matrices in combination with cells can be used for in vitro pathophysiology models for drug screening and tissue engineered constructs for regenerative medicine. As these cell-based platforms take center stage in testing, development and manufacturing of pharmaceuticals, quality control tools can be used to reproducibly generate and maintain these platforms. The fiber-optic based pH sensor is tolerated by cells and measures local pH change in a physiologically-relevant range of pH 5-8 with minimal drift in calibration over 21 days.

Three-dimensional microtissues and synthetically grown constructs are tools used in regenerative medicine and drug development. These cell-based platforms are used in testing, development and manufacturing of pharmaceuticals, and a need exists for quality control tools to test reproducibility of producing and maintaining these platforms. Sensing in active biomanufacturing environment challenges conventional sensor technology. Sensors embedded in biological medium include biocompatible materials to minimize biofouling, leaching of toxic substances from sensor surface, and to provide non-toxicity of components in contact with cell media. The sensor matches mechanical properties of the surrounding tissue environment and are durable enough to survive sterilization conditions with minimal reliability drift over many weeks to avoid re-calibration. Re-calibration can introduce foreign cells or pathogens to the cell construct. The pH photothermal spectrometer overcomes these disadvantages of conventional devices.

Conventional electrical sensors can fail to meet measurement and material science challenges involved with embedded bio-measurement specifications. Photonic sensors provide biocompatible sensors for physical, mechanical, or chemical sensing that can include an optical sensor (e.g., a florescent nanoparticle or molecular dye) or fiber optic-based sensor for chemical detection. Fiber-optic based sensors have a small probe size (e.g., 100 µm diameter) and chemical inertness.

Photothermal spectroscopy can use a fiber optic thermometer (e.g., a fiber Bragg grating (FBG)) in the pH photothermal spectrometer. The pH photothermal spectrometer includes FBGs to monitor a magnitude of thermalization of free-space propagated light absorbed by a pH sensitive chromophore (e.g., red cabbage extract). As the pH changes, light absorption (and heat generation) properties of the chromophores changes. As a result, the temperature increases upon light absorption by the chromophore that corresponds to the chromophore's UV-visible optical absorption spectrum. Ratiometric measurement of relative temperature increases measure pH of the analyte medium, and the measurement is independent of photodiode and FBG response sensitivity.

The pH photothermal spectrometer includes a photonic pH optrode in cell growth media with phenol red (PR) as a pH indicator dye. Phenol Red was added to growth media as a visual pH assay. The pH photothermal spectrometer included an uncoated FBG and PR powder. For calibration, PR powder added a buffer composition. Buffers can include citric acid, sodium citrate, acetic acid, sodium acetate, tris, CHES, and phosphate. Buffer pH was measured with a conventional pH probe. For cell-based experiments, PR powder was added to cell wash off collected after 1-3 days of cell growth. For these experiments the cells were grown in clear cell media. Blue (450 nm±5 nm, 75 mW) and green (520 nm±5 nm, 75 mW) LEDs with FC adapters were used. UV-Vis spectra were acquired.

A configuration for evaluating the temperature-increases upon illumination of pH-sensitive chromophores is shown in FIG. 10 to FIG. 13. An LED controller controlled the optical output of the LED. Optical fiber cable had a 105 µm diameter and 0.22 NA optogenetic Y-cable that delivered half of the excitation light from the LED directly to the analyte medium while the other half impinged on a photodiode for real-time measurement of LED power output. These readings were used as a correction factor in calibration.

For pH measurement, a glass tube (4 mm OD, 3 mm ID) was filled with a solution of PR. The FBG was disposed in the tube, which was aligned such that the excitation light overlapped the FBG sensor. The FBG sensor was probed with laser light that was scanned over several nanometers. The light reflected off of the FBG and measured with a power meter. Changes in temperature changed the FBG resonant wavelength, and a temperature increases resulted in a red shift of the FBG resonant wavelength while temperature decreases resulted in a blue shift. For each measurement, the FBG was interrogated for several minutes before turning on the excitation light.

Figure 11:
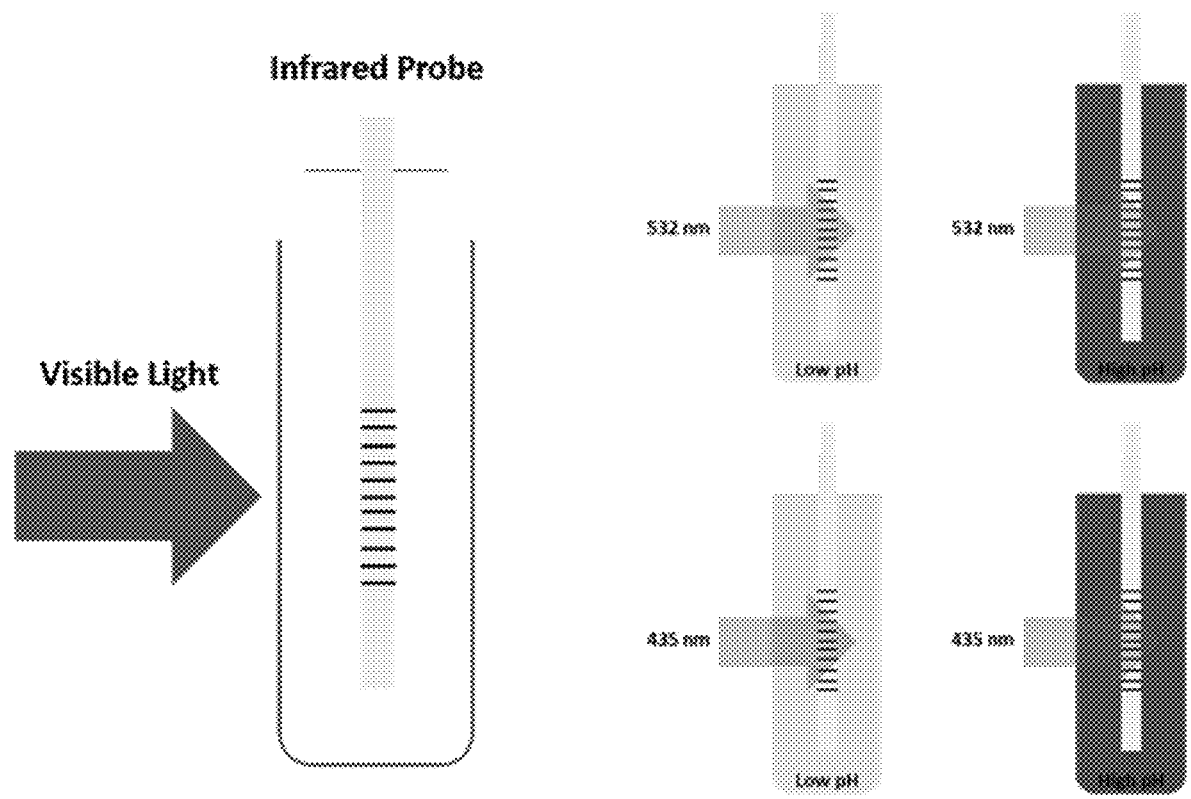
FIG. 11 shows pH photothermal spectroscopy.

More specifically, with reference to FIG. 11, a small amount of pH indicator dye (red cabbage extract) was dissolved in a buffered solution of known pH value. The solution (0.1 ml to 1 ml) was then filled into the glass tube and an FBG sensor inserted into the tube, A 0.22 NA fiber carrying excitation light was placed orthogonal to the FBG such that the light cone exiting the fiber enveloped the FBG temperature sensor. At the excitation light source red and green lights were periodically turned on and off for several minutes and the FBG spectra was recorded for both the "on" and "off" state. The relative rise in temperature was measured by measuring the shift in wavelength center of the FBG response curve. The ratio of wavelength shift for both red and green excitation was then calculated. From pH 2.5 to 10, the ratio of wavelength shift (i.e. temperature rise) for green and red excitation was plotted and a linear regression was employed to calculate a calibration model. The calibration model has the form of $pH=\{[\Delta\lambda_{red}/\Delta\lambda_{green}]-b\}/S$; where S and b are calculated using linear regression on calibration data. To determine the pH of unknown solution, the $\Delta\lambda_{red}/\Delta\lambda_{green}$ is measured and the values of S and b parameter are used to calculate the solution pH.

Figure 12:
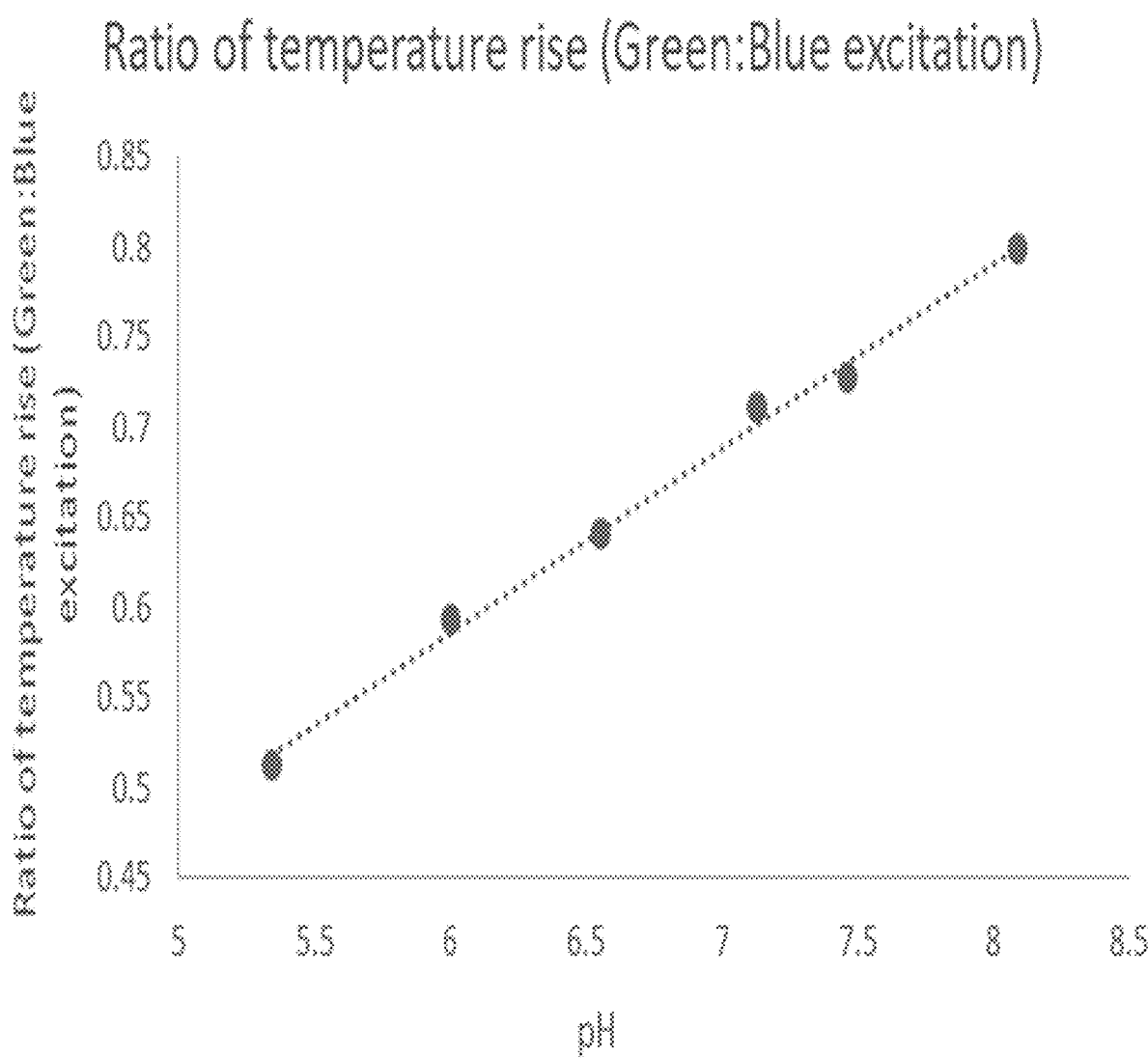
FIG. 12 shows a graph of normalized signal versus pH for phenol red.
Figure 13:
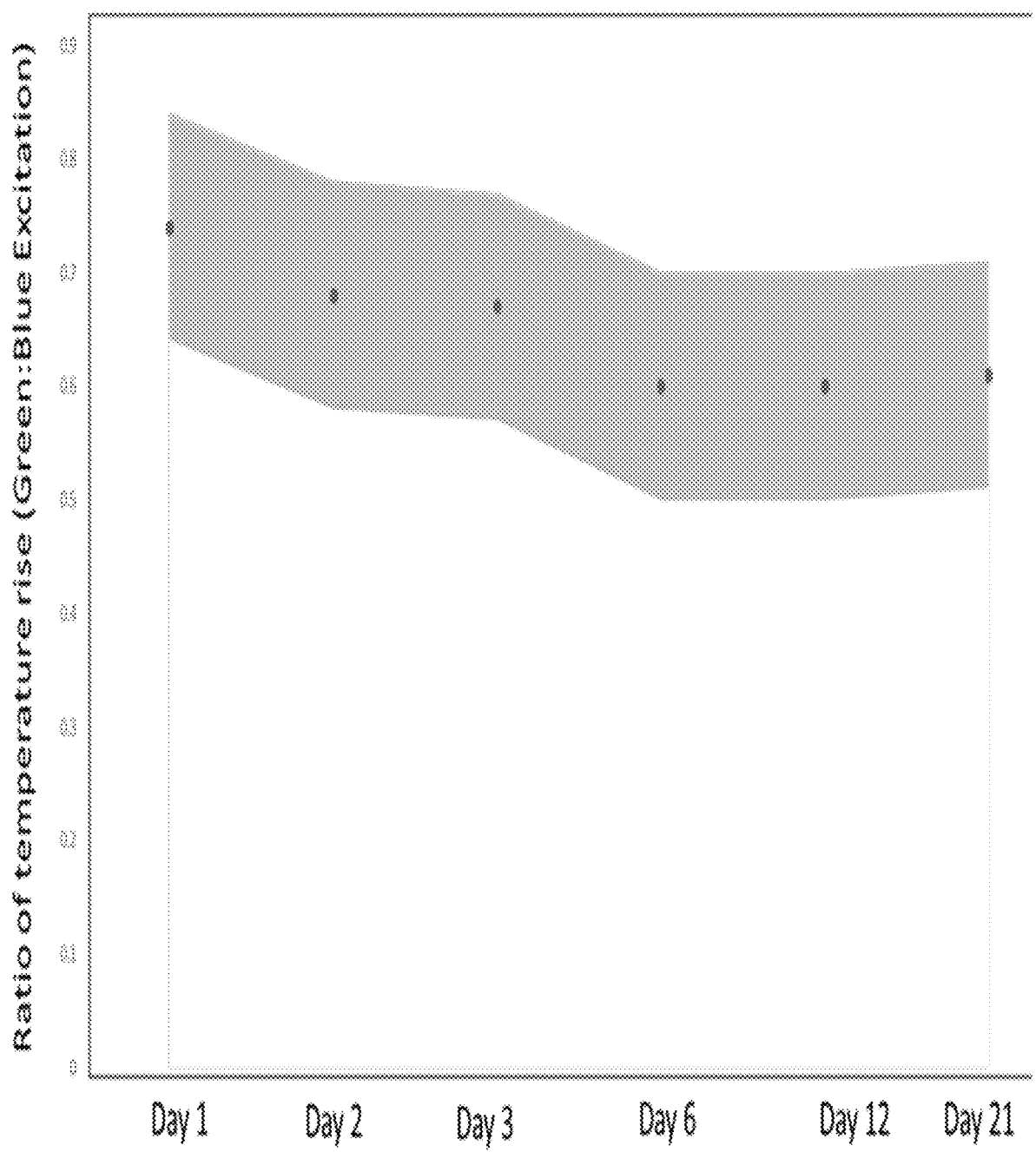
FIG. 13 shows a graph of normalized signal versus time for phenol red.

Results of measurements are shown in FIG. 12 and FIG. 13. As shown in FIG. 12, a ratio of temperature rise at green and blue excitation light was collected a function of pH. Here, a small amount of pH indicator dye (phenol red) was dissolved in a buffered solution of known pH value. 0.1 ml to 1 ml of the prepared solution was then filled into the glass tube and an FBG sensor inserted into the tube, A multimode fiber carrying excitation light was placed orthogonal to the FBG such that the light cone exiting the fiber enveloped the FBG temperature sensor. At the excitation light source blue and green lasers were periodically turned on and off for several minutes and the FBG spectra was recorded for both the "on" and "off" state. The relative rise in temperature was measured by measuring the shift in wavelength center of the FBG response curve. The ratio of wavelength shift for both red and green excitation was then calculated. Over the pH range of 5 to 8, the ratio of wavelength shift (i.e. temperature rise) for green and red excitation was plotted and a linear regression was employed to calculate parameters of the calibration model.

With reference to FIG. 13, repeat measurements of a pH solution with the same probe were made over a 2-week period. Here, phenol red was dissolved in pH 6.7 buffered solution. The pH of the buffered solution was then measured using a standard electronic pH probe. A small amount of the buffered solution with phenol red was placed in the apparatus and ratio metric measurement of wavelength shift under green and blue excitation were made for 21 consecutive days. These measurements indicate the pH of the solution as measured by ratiometric method does not show any significant changes over the course of 3 weeks.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. A pH photothermal spectrometer for performing pH photothermal spectroscopy, the pH photothermal spectrometer comprising:
  a container comprising an interior bounded by a wall of the container, such that container:
    receives an analyte medium and a pH-sensitive chromophore, the pH-sensitive chromophore comprises an optical absorption spectrum that adjusts to a pH of the analyte medium, the analyte medium comprising an analyte temperature; and
    optionally receives a fiber encapsulation matrix in which are disposed the analyte medium and the pH-sensitive chromophore;
  an excitation fiber disposed in the container in optical communication with the pH-sensitive chromophore and that:
    receives a first excitation light comprising a first wavelength and a second excitation light comprising a second wavelength; and communicates the first excitation light and the second excitation light to the pH-sensitive chromophore, such that the pH-sensitive chromophore:
receives the first excitation light and the second excitation light; and
absorbs a first amount of the first excitation light and a second amount of the second excitation light based on the pH of the analyte medium such that absorption of the first excitation light or the second excitation light increases the analyte temperature of the analyte medium; and
an optical thermometer disposed in the container and comprising:
a temperature detector fiber that
receives a probe light comprising a probe light wavelength in a first optical amount; and
receives a reflected light comprising the probe light wavelength from a light receiver; and
the light receiver:
disposed on a terminus of the temperature detector fiber in optical communication with the temperature detector fiber and in thermal communication with the analyte medium; and
comprising:
a receiver temperature that adjusts to match the analyte temperature; and
an optical resonance at a resonance wavelength that changes in response to a change in the receiver temperature,
such that the light receiver:
receives the probe light from the temperature detector fiber;
produces, from the probe light, a reflected light in a second optical amount and comprising the probe light wavelength, such that the second optical amount of the reflected light depends on the receiver temperature of the light receiver, so that a ratio of the first optical amount to the second optical amount provides the pH of the analyte medium; and
communicates the reflected light to the temperature detector fiber; and
the temperature detector fiber receives the reflected light from the light receiver.

2. The pH photothermal spectrometer of claim 1, further comprising a fiber port disposed on the container through which is disposed the optical thermometer.

3. The pH photothermal spectrometer of claim 1, further comprising a fiber port disposed on the container through which is disposed the excitation fiber.

4. The pH photothermal spectrometer of claim 1, comprises the fiber encapsulation matrix that encapsulates the light receiver, the excitation fiber, or a combination comprising at least one of the light receiver and the excitation fiber.

5. The pH photothermal spectrometer of claim 1, wherein the fiber encapsulation matrix maintains a position of the excitation fiber and the light receiver in the container.

6. The pH photothermal spectrometer of claim 1, wherein the fiber encapsulation matrix comprises a gel.

7. The pH photothermal spectrometer of claim 1, wherein the pH-sensitive chromophore is subject to diffusion in the analyte medium.

8. The pH photothermal spectrometer of claim 1, wherein the pH-sensitive chromophore is disposed in the fiber encapsulation matrix via entropic trapping, covalent bond attachment, or electrostatic trapping.

9. The pH photothermal spectrometer of claim 1, wherein the light receiver comprises a fiber Bragg grating, an on-chip thermometer, a Raman fiber optic thermometer, a Brillouin fiber optic thermometer), or a fluorescent particle.

10. The pH photothermal spectrometer of claim 1, wherein the light receiver is the fluorescent particle that comprises a nitrogen vacancy diamond.

11. The pH photothermal spectrometer of claim 1, wherein the analyte medium comprises a cell medium.

12. The pH photothermal spectrometer of claim 1, further comprising an excitation light source in optical communication with the excitation fiber and that provides the first excitation light to the excitation fiber.

13. The pH photothermal spectrometer of claim 1, further comprising a probe light source in optical communication with the temperature detector fiber and that provides the probe light to the temperature detector fiber.

14. The pH photothermal spectrometer of claim 1, further comprising a detector in optical communication with the temperature detector fiber and that receives the reflected light from the optical thermometer.

15. The pH photothermal spectrometer of claim 1, wherein the temperature detector fiber extends into and out of the interior of the container in a plurality of locations of the wall of the container.

16. The pH photothermal spectrometer of claim 1, wherein the excitation fiber is disposed orthogonal to the optical thermometer in the container, parallel to the optical thermometer in the container, or at an oblique angle with respect to the optical thermometer.

17. The pH photothermal spectrometer of claim 1, wherein the excitation fiber comprises an optical taper disposed at a terminus of the excitation fiber proximate to the light receiver.

18. A process for performing pH photothermal spectroscopy with the pH photothermal spectrometer of claim 1, the process comprising:
receiving, by the excitation fiber, the first excitation light that comprises the first wavelength and the second excitation light that comprises the second wavelength;
contacting the pH-sensitive chromophore with the analyte medium;
adjusting the optical absorption spectrum of the pH-sensitive chromophore in response to the pH of the analyte medium;
communicating the first excitation light and the second excitation light from the excitation fiber to the pH-sensitive chromophore;
receiving, by the pH-sensitive chromophore, the first excitation light and the second excitation light;
absorbing, by the pH-sensitive chromophore, the first amount of the first excitation light based on the pH of the analyte medium;
absorbing, by the pH-sensitive chromophore, the second amount of the second excitation light based on pH of the analyte medium;
adjusting the analyte temperature of the analyte medium in response to the pH-sensitive chromophore absorbing the first excitation light and the second excitation light;
adjusting the receiver temperature of the light receiver to match the analyte temperature of the analyte medium in response to adjusting the analyte temperature of the analyte medium;
receiving, by the light receiver, the probe light in the first optical amount from the temperature detector fiber;
producing, by the light receiver from the probe light, the reflected light in the second optical amount that depends on the receiver temperature of the light receiver, the reflected light comprising the probe light wavelength; and determining the pH of the analyte medium from a ratio of the first optical amount to the second optical amount to perform pH photothermal spectroscopy.

19. The process of claim 18, further comprising:

communicating, from the light receiver, the reflected light to the temperature detector fiber; and receiving, by the temperature detector fiber, the reflected light from the light receiver.

20. The process of claim 18, further comprising: calibrating the pH photothermal spectrometer so that the second optical amount provides a pH of the analyte medium.

* * * * *